(12) United States Patent
Skillman et al.

(10) Patent No.: US 6,375,904 B1
(45) Date of Patent: Apr. 23, 2002

(54) WASTEWATER COLLECTION SYSTEM GAS EMISSION CONTROL

(75) Inventors: David B. Skillman, Franklin; Henry A. Berman, Indianapolis; William C. Weaver, Carmel, all of IN (US)

(73) Assignee: Airtex Manufacturing, Inc., DeSoto, KS (US)

( * ) Notice: Subject to any disclaimer, the term of this patent is extended or adjusted under 35 U.S.C. 154(b) by 0 days.

(21) Appl. No.: 09/467,187

(22) Filed: Dec. 20, 1999

(51) Int. Cl.⁷ .......................... A61L 9/015; B01D 53/34
(52) U.S. Cl. .................. 422/172; 422/169; 422/171; 422/174; 422/186.07; 422/121
(58) Field of Search ................. 422/168–172, 422/121, 173, 174, 186.07, 177

(56) References Cited

U.S. PATENT DOCUMENTS

| | | | |
|---|---|---|---|
| 3,937,967 A | * 2/1976 | Steintz | 250/435 |
| 3,954,586 A | 5/1976 | Lowther | |
| 3,984,697 A | 10/1976 | Lowther | |
| 4,110,086 A | 8/1978 | Schwab et al. | |
| 4,317,044 A | 2/1982 | Vaseen | |
| 5,145,657 A | 9/1992 | Kobayashi et al. | |
| 5,160,481 A | * 11/1992 | Weaver | 422/186.07 |
| 5,173,268 A | 12/1992 | Weaver | |
| 5,368,816 A | * 11/1994 | Detzer | 422/172 |
| 5,433,854 A | * 7/1995 | Dickerson | 210/620 |
| 5,578,211 A | 11/1996 | Dickerson | |
| 5,578,280 A | 11/1996 | Kazi et al. | |
| 5,601,786 A | 2/1997 | Monagan | |
| 5,751,007 A | 5/1998 | Weaver | |

OTHER PUBLICATIONS

Linus Pauling *General Chemistry* Dover Publications, Inc. N.Y. ISBN 0–486–65622–5 (pbk.), p. 754, 1988.*
Odor Control System for Wastewater Pump Stations, Lift Stations and Treatment Plants (From Internet research) no date.

* cited by examiner

*Primary Examiner*—Hien Tran
(74) *Attorney, Agent, or Firm*—Brinks Hofer Gilson & Lione

(57) ABSTRACT

A wastewater collection system is provided with a gas withdrawal vent including a gas suction apparatus. The gas is preferably withdrawn at a rate in excess of the gas production by microbes in the wastewater collection system so that a slight negative pressure is created in the immediate vicinity of the gas withdrawal vent. A gas mixing chamber is coupled to the fan or blower to receive the gas withdrawn from the wastewater collection system. An ozone generation apparatus is also coupled to the gas mixing chamber that is adjusted to provide sufficient ozone to react with any noxious or malodorous components of the withdrawn gas. A reaction conduit is provided at an output of the gas mixing chamber to receive the withdrawn gas and ozone. The reaction conduit has surface features assuring turbulent flow of the gasses through the length of the conduit. The reaction conduit is also of sufficient length as to assure complete decomposition and removal of the noxious or malodorous components from the withdrawn gas, and reduction of the ozone to a negligible concentration in the gas emitted from the reaction conduit.

8 Claims, 4 Drawing Sheets

WASTEWATER COLLECTION SYSTEM GAS EMISSION CONTROL

BACKGROUND OF THE INVENTION

The present invention is directed generally to the control of undesirable odors typically generated by microbial activity in waste water systems. The present invention is particularly directed to the reduction of such undesirable odors in the immediate vicinity of wastewater lift stations, pumping stations, and other pretreatment facilities.

Modern wastewater collection systems, often referred to as sewage systems, are designed to capture and transport effluent from sources such as homes, schools, offices and factories to a common wastewater treatment facility. At the treatment facility, the wastewater is biologically and chemically treated so that the water can be released back into the environment with as little impact as possible. Treatment facilities are generally open to the atmosphere to promote aerobic microbial processes to biologically reduce the undesirable characteristics of the wastewater, and for that reason are typically situated in remote, thinly populated areas. The collection system leading to the treatment facility typically is a generally closed system of pipes, except at certain selected points, so as to inhibit dilution of the wastewater by runoff due to local rain showers or snow melt. The generally closed nature of the system is also intended to prevent any unwanted dispersal of the wastewater into the environment prior to proper treatment at the treatment facility.

Pretreatment facilities such as lift stations and pumping stations are typically included in the collection system at selected points to gather and pump wastewater to a next station and, ultimately, to a waste treatment plant. The pretreatment facilities typically include a large concrete pit with a number of incoming pipes carrying wastewater. A pump situated in the pit or wet well is coupled to an outflow pipe. The pump is generally controlled by switches that are responsive to the level of liquid in the pit. Generally, the pumps operate periodically, rather than continuously, with the level of wastewater in the pit falling during times that the pump is operating and rising when the pump is not operating. When the pumps are not operating and the wastewater is accumulating, there is more opportunity for the accumulation of significant populations of microbes that produce gases including hydrogen sulfide, methyl sulfide, methyl disulfide, mercaptans such as methyl mercaptan, ammonia, methylamines including di- and trimethylamine, various ethylamines and butylamines, pyridine, acetone, ketone, phenol, benzene, methane, butene, toluene, and many others, much of which is malodorous, noxious, and in some circumstances, dangerous to human health and welfare. The principal offensive gas present is generally hydrogen sulfide.

The frequent changes in liquid level in the wet wells of such pretreatment facilities requires the existence of vents that will permit entry of air into the pit as the wastewater level falls. As the level of wastewater rises, the gases that accumulate above the wastewater are often released out the same vents into the atmosphere. Since the wastewater lift stations, pumping stations, and other pretreatment facilities are sometimes situated in the immediate neighborhood of human habitations, the release of such gases can be much to the disgust of the local human inhabitants. The odors can be very strong especially if the accumulation period between pumping operations is long, or during summer when the temperatures are hot for extended periods thus encouraging the growth of microbial populations. The total prevention of gas release at such pretreatment facilities is generally not a realistic option. The treatment of such released gas so as to reduce its offensive character is a realistic option that has gained the attention of others previously.

It has been recognized that such noxious and malodorous gasses are treatable generally by an application of ozone as discussed, for example,. in Kobayashi, et al., U.S. Pat. No. 5,145,657 and Monagan, U.S. Pat. No. 5,601,786. A variety of equipment exists that can be used to generate ozone including, for example, Lowther, U.S. Pat. Nos. 3,954,586; 3,984,697; and 3,996,474; Schwab, et al., U.S. Pat. No. 4,110,086; Vaseen, U.S. Pat. No. 4,317,044; Weaver, U.S. Pat. Nos. 5,160,481; 5,173,268; and 5,751,007; and Kazi, et al., U.S. Pat. No. 5,578,280. Specifically, it has been previously suggested in Dickerson, U.S. Pat. Nos. 5,433,854 and 5,578,211, that such noxious and malodorous gasses might be eliminated from wastewater systems by an introduction of ozone into the system at various points together with the maintenance of a minimum level of nitrogen. It will be appreciated by those skilled in the art that the forced introduction of any gas within a closed space must result in either an elevated pressure within that space or the displacement of a like quantity of the same or another gas from that space through any available vent. As a practical matter, recognizing that no wastewater collection piping system is completely sealed, it has been found that the forced introduction of ozone into a wastewater collection piping system, as suggested by Dickerson, merely enhances the displacement of the noxious and malodorous gasses out of available vent points, much to the displeasure and potential harm of persons in the vicinity of the vents. Further, the introduction of the ozone into the system, at selected points such as lift stations and the like, must be very carefully controlled to avoid significant and substantial erosion of portions of the system by the highly oxidative ozone itself.

It has also been recognized that such noxious and malodorous gasses are treatable generally by withdrawing the gasses from the wet well and passing the gases through a bed of activated carbon. The carbon bed will operate satisfactorily for a period of time, however, periodically it must be replaced, and the spent carbon disposed of as required by law, typically at a hazardous waste facility. It has also been recognized that the replacement schedule for such carbon beds can be extended by exposing the activated carbon bed to a stream of ozone. Such equipment is available from Parson Environmental Products of Reading, Pennsylvania under the trademark carbOzone. This equipment is not satisfactory in that it is unable to eliminate odor "spikes" occurring during certain periods and requires the periodic disposal of the spent carbon. Furthermore, it is known that activated carbon and ozone can become unstable, and pose an explosion-fire hazard if ozone concentrations exceed 0.3%. Thus, the exposure of carbon beds to ozone should only occur under tightly controlled and monitored conditions that are generally not found in typical wastewater pretreatment facilities, which are generally unmanned facilities.

It is therefore desirable to construct a facility for treatment of gasses from wastewater lift stations, pumping stations, and other pretreatment facilities that will accommodate such odor "spikes" and does not require the disposal of any materials, particularly hazardous waste materials, does not pose an explosion-fire hazard, and emits no ozone into the atmosphere.

SUMMARY OF THE INVENTION

In accordance with the present invention, apparatus is connected to a vent of a wastewater pretreatment facility including a gas suction apparatus such as a fan or blower. The gas is withdrawn at a rate in excess of the gas production by microbes in the wastewater collection system so that the wet well of the wastewater pretreatment facility is maintained at a slight negative pressure. The gas withdrawn from the pretreatment facility is introduced by the fan or blower into a mixing chamber. An ozone generation apparatus is also coupled to the mixing chamber and provides a controlled supply of ozone, generally created electrically from the ambient air, to the mixing chamber. The ozone generation apparatus is adjusted to provide sufficient ozone to react with any noxious or malodorous components of the withdrawn gas even during peak production periods. A reaction conduit is coupled to the reaction chamber to receive the withdrawn gas and ozone. The reaction conduit is chosen to have surface features assuring turbulent flow of the gasses through the length of the conduit and to have sufficient length as to assure substantially complete decomposition and removal of the noxious or malodorous components from the withdrawn gas.

While the present invention has particular utility in connection with the reduction of odorous gasses from wastewater pretreatment facilities, the apparatus can be employed in similar fashion to treat a broad assortment of odorous gasses that may be present in a wide variety of facilities from which a controlled withdrawal of gas can be achieved, such as hog feeding enclosures and rendering plants. The invention includes the method of reducing the free release of odorous gasses by withdrawing the odorous gasses from an enclosed space at a controlled rate, mixing the withdrawn odorous gasses with a measured amount of ozone, and directing the mixed gases through a reaction conduit chosen to have surface features assuring turbulent flow of the gasses through the length of the conduit and to have sufficient length as to assure substantially complete decomposition and removal of the noxious or malodorous components from the withdrawn gas.

One desirable feature of the present invention is the specific provision of an reaction conduit that is designed to facilitate maximum mixing of the ozone and the withdrawn gasses to maximize their interaction. The reaction conduit is preferably constructed of an inexpensive and generally non-reactive material that is commonly available such as corrugated plastic pipe.

Another desirable feature of the present invention is the addition of an ozone sensor near an output of the reaction conduit to monitor the output to ensure that no overproduction of ozone is permitted, which might cause a free release of ozone into the environment. One or more additional sensors can be included at intermediate positions along the length of the reaction conduit to monitor the ozone level and, if appropriate, control the level of ozone produced by the ozone generation apparatus.

Still another desirable feature is a heated terminal reduction chamber located at the output of the reaction conduit that operates to reduce any residual ozone to ordinary oxygen prior to release into the atmosphere.

Still other features and advantages of the present invention will become apparent to those skilled in the art from a consideration of the following description of a preferred embodiment of the present invention illustrated in the accompanying figures.

DESCRIPTION OF THE ILLUSTRATED EMBODIMENT

Figure 1:
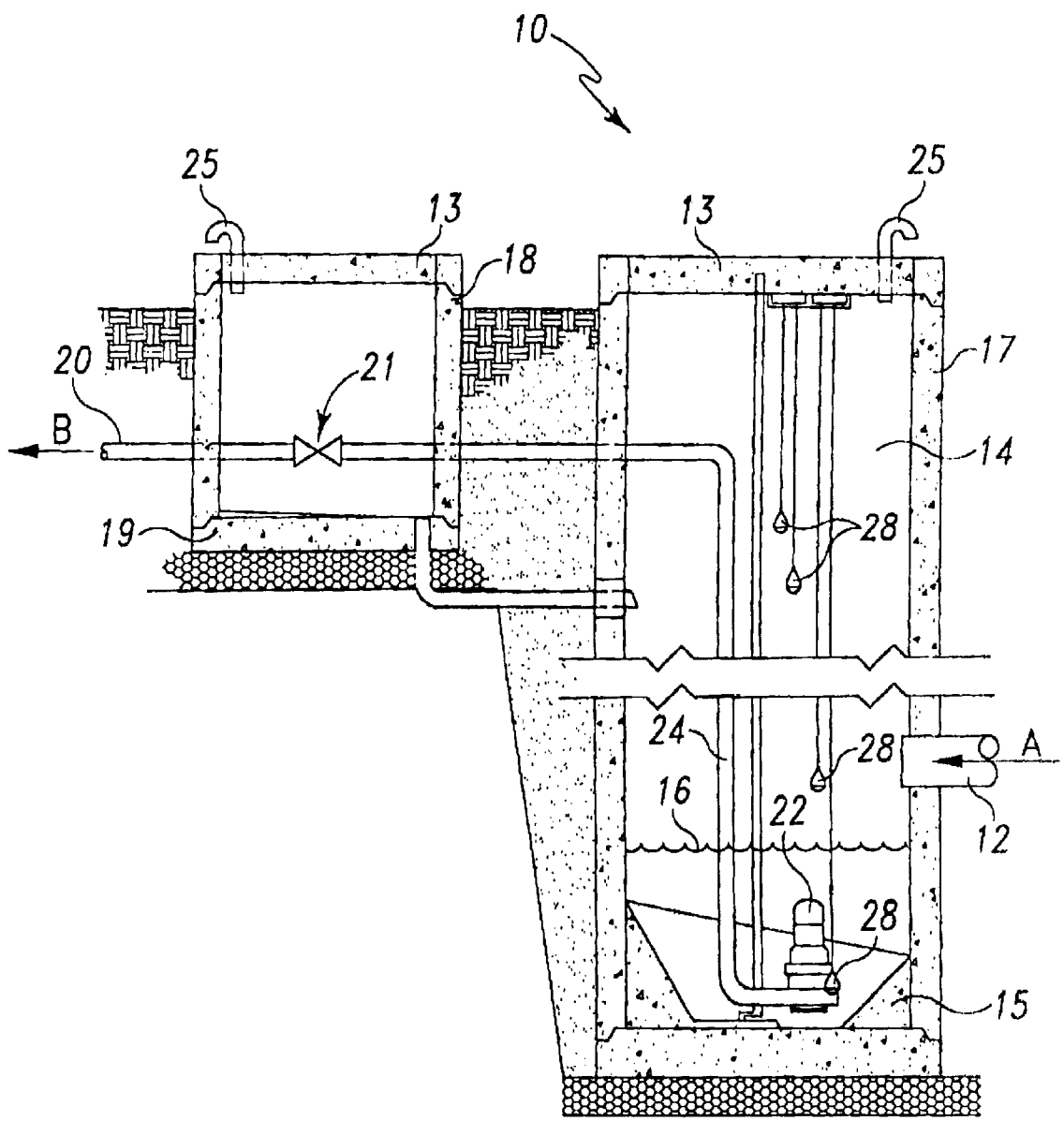
FIG. 1 is a schematic view of a typical wastewater lift station to which the present invention can be applied.

A typical wastewater lift or pumping station 10 to which the present invention can be applied is shown in FIG. 1. An underground wastewater collection system is shown to comprise one or more inflow pipes 12 in which wastewater travels, generally by gravity, in the direction of arrow A into a wastewater wet well 14. The wet well 14 includes a floor 15 and side walls 17 that are sealed so that the wastewater delivered to the wet well is unable to drain or seep from the wet well. The wet well 14 can be of any size or depth sufficient to hold a volume of wastewater which may be delivered to the lift station 10 over a convenient period of time of up to perhaps an hour or even longer. While the present illustrated embodiment of the invention is related directly to the lift station 10, it will be understood that the invention can be employed with any other type of intermediate or even final processing location in the wastewater collection system where odorous gasses might accumulate, or to reduce the free release of odorous gasses from other facilities such as animal enclosures, rendering plants, etc.

The lift station 10 also generally includes an upper chamber or valve pit 18 having a floor 19 and an outlet or forced drain pipe 20 carrying the wastewater away from the lift station 10 in the direction of arrow B. The valve pit 18 commonly contains certain cutoff and safety valves 21 that can control the flow of the wastewater away from the lift station 10. A pump 22 is provided to pump the wastewater from the wet well 14 into the forced drain pipe 20 through the valves 21 in valve pit 18. The pump 22 is shown to comprise a submersible pump coupled to piping 24 leading from the wet well 14 to the upper chamber 18. A submersible pump 22 could of course be replaced with merely a submersible impeller driven by a remote pump motor (not shown) positioned near the top of the wet well 14.

The lift station 10, including both the wet well 14 and the valve pit 18, is provided with vents 25 shown to be positioned in the top 13 of the lift station 10. The submersible pump 22 or pump motor is responsive to a plurality of wastewater level sensors 28 shown to be positioned in wet well 14 to cause the pump motor to operate on an "as needed" basis to keep the level of the wastewater in wet well 14 below a prescribed level. When the pump motor is operative, it causes the wastewater 16 within wet well 14 to be pumped through piping 24 away from the pumping station 10. In the absence of the present invention, as the level of wastewater in the wet well 14 falls, air is pulled into the wet well through one or more vents 25. Once the pumping ceases, and as wastewater is introduced into the wet well 14 through the one or more inflow pipes 12, the atmosphere above the wastewater is caused to flow out the vents 25 due to the rising level of wastewater in the wet well 14.

Figure 2:
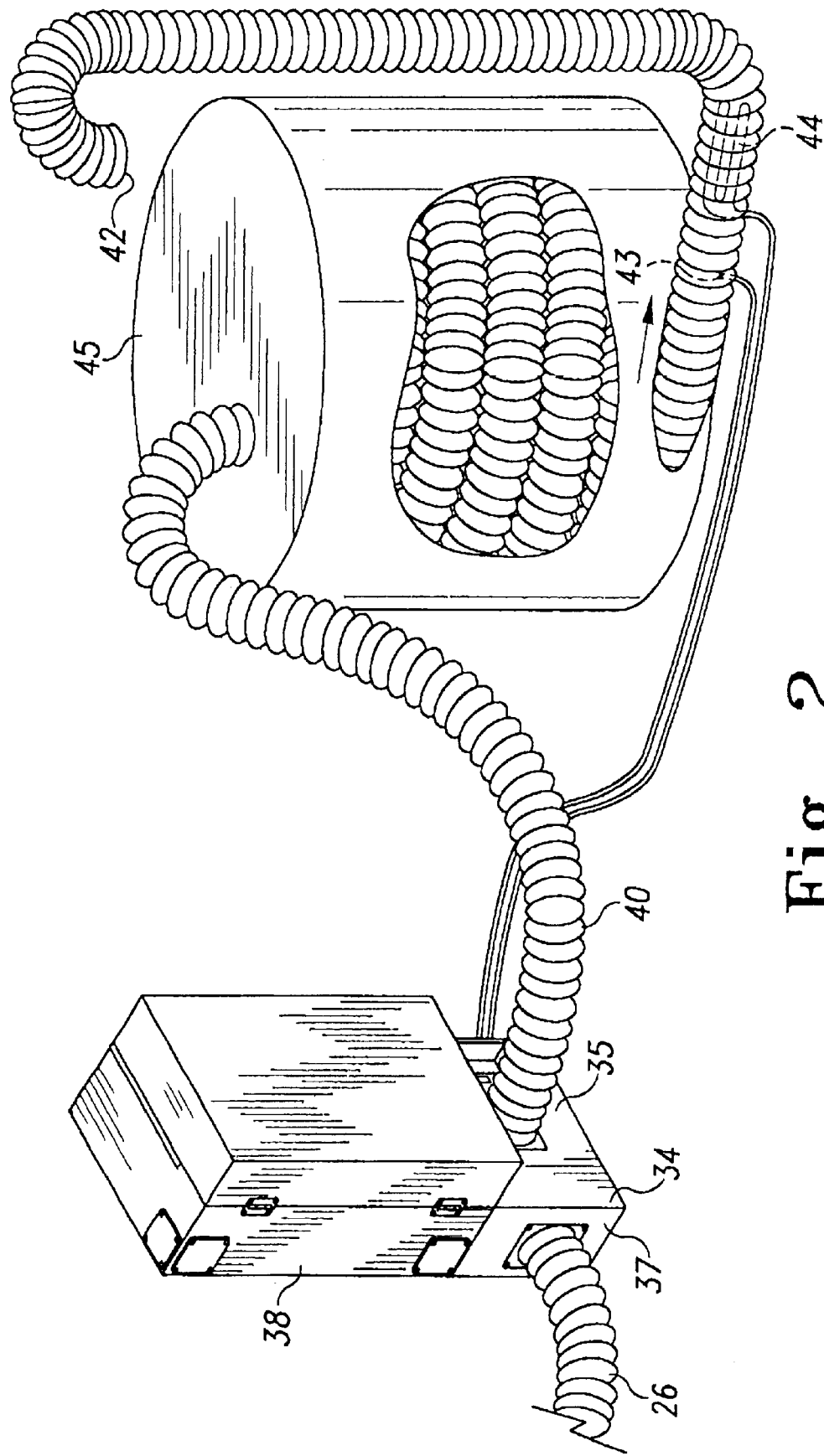
FIG. 2 is a perspective view of an apparatus of the present invention.

The volume within the lift station 10 which is above the level of the wastewater 16 is filled with an atmosphere that, in the absence of the present invention, is filled with noxious gases of various types which are generated as a result of biological reactions occurring at the microbial level within the wastewater 16 and on surfaces of the lift station 10 in contact with the wastewater 16. Since it is not practical to seal the lift station 10, the gas easily escapes through the vents 25 and other openings to contaminate the surrounding atmosphere. To prevent this, the present invention, shown in FIG. 2, is coupled to at least one of the vents 25 of the lift station 10 or other facility from which a reduction in the free release of odorous gasses is desired.

In accordance with the present invention, one or more vents 25 are coupled to a duct 26 leading to a fan or other suction device 34. The suction device 34 is generally supplied with power on a substantially continuous basis to ensure an outflow of gas from the lift station 10 into the apparatus of the present invention. Any of the vents 25 at the lift station 10 that are not coupled to the duct 26 can be supplied with a check valve for allowing the intake of air from the atmosphere into the wastewater lift station while preventing an outflow of gas directly to the atmosphere from the lift station 10. The suction device 34 is operated at such a speed as will withdraw air and gas from the wastewater lift station in such volume as to at least equal the volume of noxious gas being biologically created in the wastewater collection system and lift station. From a practical matter, the volume of gas withdrawn by suction device 34 can be controlled by controls 41 provided on the face of housing 37. The volume is preferably such as to insure at least a modest inflow of air through any available open vents 25, or if no vents are available, to insure the lift station is subjected to a slight negative pressure except during periods of peak wastewater inflow into the wet well 14 when the gas displacement by the wastewater inflow may be sufficient to offset any slight negative pressure. The suction device 34 includes an output that is coupled to an initial mixing chamber 35 that is situated within the same housing 37 as the suction device 34. The initial mixing chamber 35 also includes an intake 36 that is coupled to an output of an ozone source or generator 38.

The ozone source or generator 38 generally develops ozone in sufficient quantity to react with all of the noxious components of the gas withdrawn by fan 34. The withdrawn gas passes through the initial mixing chamber 35 where it is intimately mixed with the ozone and thereafter introduced into a reaction chamber 40. The reaction chamber 40 is of sufficient length to provide ample opportunity for the necessary chemical reactions to take place between the ozone and the complex organic components of the withdrawn gas so that by the time the gas exits from the reaction chamber through exit 42, the gas no longer carries a discernible odor from noxious components. In a preferred embodiment, the reaction chamber 40 comprises at least about 30 linear feet of 6 inch diameter corrugated plastic pipe that can be curled within a drum 45, which can be made of polyethylene or other suitable resin, and situated either above or below ground level immediately adjacent to the ozone generator 38. An ozone sensor 43 can be positioned near exit 42 of the linear reaction chamber 40 to measure the level of the ozone present in the flow of gas near the exit end of the reaction chamber. The ozone sensor 43 is preferably coupled to a control for the ozone generator to provide information that can be employed to modify the level of ozone generated by the ozone generator 38. It the preferred embodiment, an electric heater 44 can be situated in the reaction chamber 40 near the exit 42 to heat the gas flowing through the reaction chamber 40 preferably to about 150° F. to accelerate the reduction of any remaining un-reacted ozone to ensure that no free release of ozone into the environment occurs.

Figure 3:
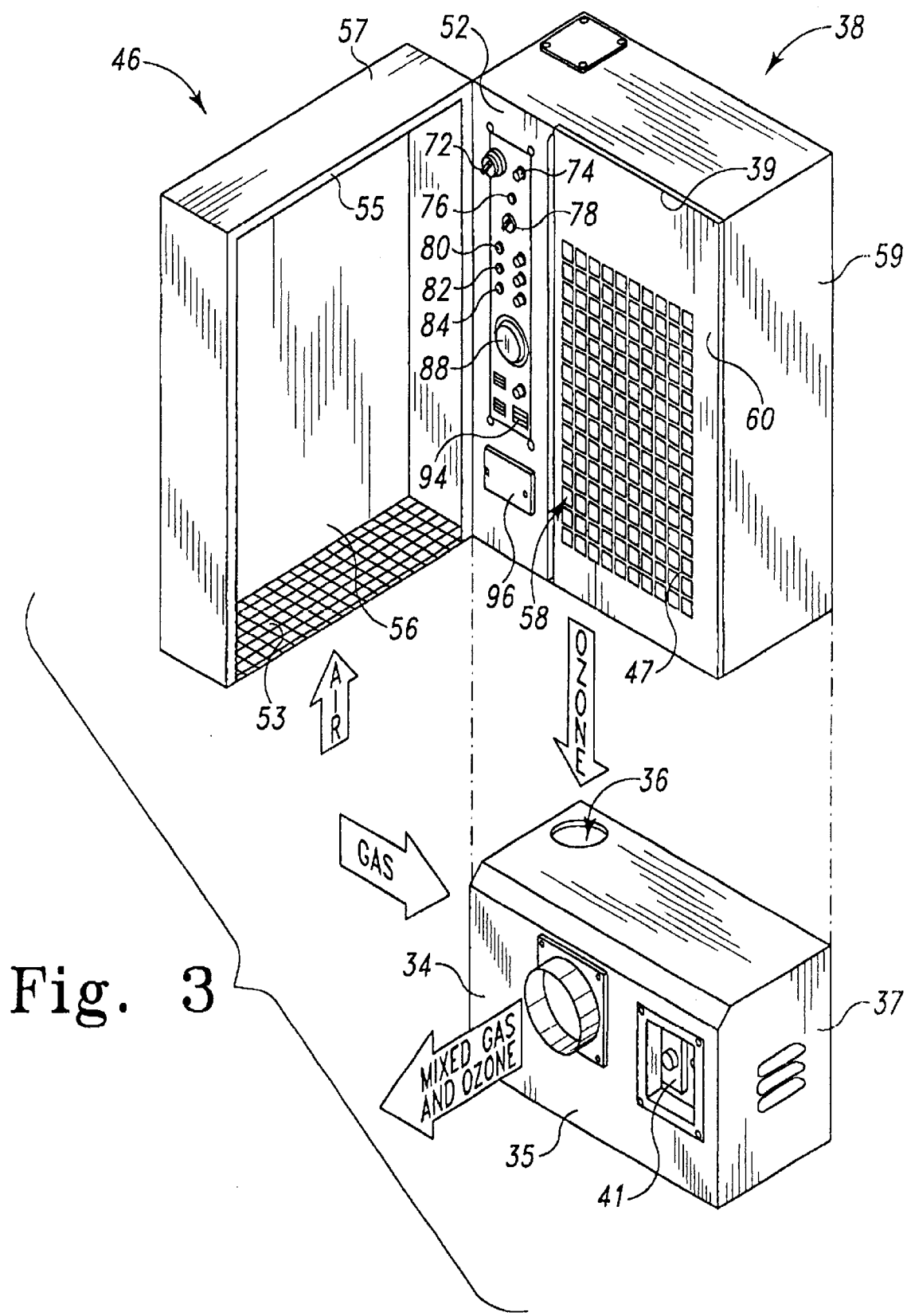
FIG. 3 is an exploded perspective view of the ozone generator and mixing chamber shown in FIG. 2.
Figure 4:
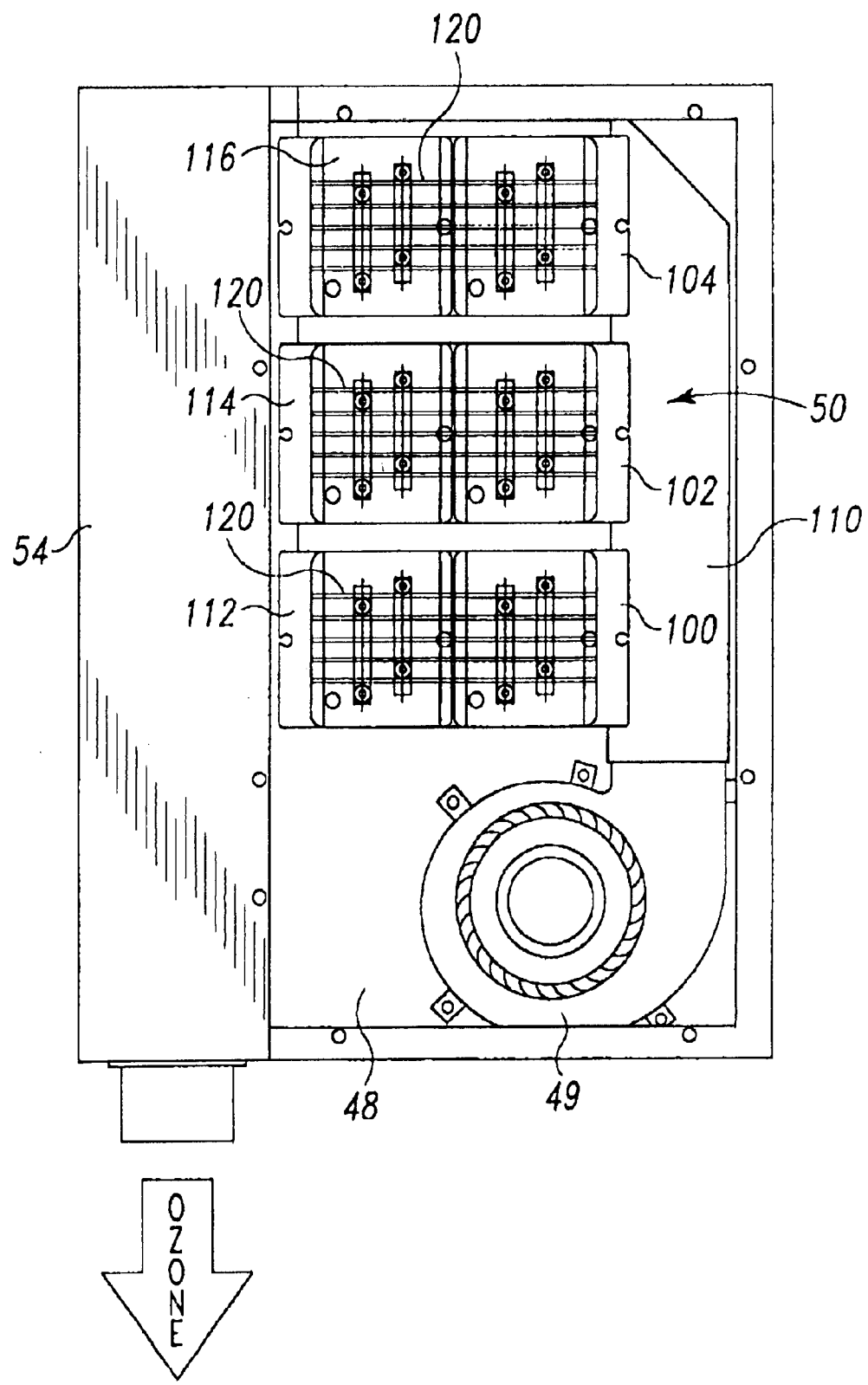
FIG. 4 is a front elevation view of the interior of the ozone generator shown in FIGS. 2 and 3.

A preferred embodiment of the ozone generator 38 is shown in FIGS. 3–4. The generator 38 comprises five major components: an intake portion 46, a fan chamber 48, an ozone generating section 50, an electrical power supply section 52 and an output chamber 54. The intake portion 46 includes a generally rectangular chamber 56 defined by a cover 57 that can be pivotally mounted to the front of ozone generator 38 by means of hinges, not shown. An edge 55 of the cover 57 seals with the perimeter 39 of the generator cabinet 59 to protect the ozone generator apparatus 38 from inclement weather. The cover 57 also covers the operating controls of the electrical power supply section 52 of the generator apparatus 38 to insure no unauthorized operation of the apparatus 38. The rectangular chamber 56 includes a lower opening 53 through which atmospheric air is taken in. The intake air then passes from chamber 56 through a grill 47, which can include a filter 58, forming a part of front wall 60 of the generator cabinet 59. The filter 58 is intended to remove droplets of moisture and other macroscopic elements from the intake air as it is drawn into the ozone generator apparatus 38.

The air is drawn into chamber 56, and through grill 47 and filter 58 by a suction fan 49 in the fan chamber 48. The output from fan 49 is directed toward the right extreme portion of the ozone generating portion 50, detailed in FIG. 4, which includes a plurality of ozone generator heads 100–104. Power is supplied to the ozone generator heads 100–104 by the electrical power supply section 52. Preferably the power to each of the ozone generator heads 100–104 can be individually controlled so that the amount of ozone generated is carefully controlled. In the preferred embodiment the ozone generator 38 typically develops about 1.7 grams/hr of ozone, and can be adjusted to produce anywhere from 0.1 to 4.8 grams/hr. Additional ozone generation capacity can be achieved through the addition of additional generator heads up to at least 10 grams/hr.

This control is provided through a main power switch 72, shown in FIG. 3, controlling power to the entire unit of the generator 38. An indication as to the presence of the power is given by power indicator 74. A safety circuit breaker reset switch 76 is also provided which controls the power to the entire device of the generator 38. A fan speed switch 78 controls the speed at which fan 49 operates to insure that the volume of air drawn into the ozone generator is appropriate for the volume of gas being withdrawn from the wastewater handling facility by suction device 34. Immediately below the fan speed switch 78 is a series of off/on switches 80, 82, 84 that control the power to the individual ozone generator heads 100, 102, 104. A master variac 88 is provided that controls the level of current to all of the generator heads 100, 102, 104 which controls the level of ozone being generated by the system as a whole. A clock 94 is provided for recording the hours of operation of the system as is an input 96 for further automatic control of the ozone generator predicated on other sensors such as sensor 43 shown in FIG. 2. It will be appreciated that the number of generator heads is merely a choice of design depending upon the volume of ozone required to neutralize the noxious components of the gas withdrawn from the wastewater handling facility by means of suction device 34.

The air taken in by fan 49 goes into a right side portion 110 of section 50. It then proceeds through one of a plurality of horizontal chambers 112, 114, 116. Each of the chambers 112, 114, 116 receives the working portion of the ozone generator heads 100, 102, 104 including a plurality of horizontal plates 120 which act to electrically generate the ozone from the free oxygen in the air passing through the horizontal chambers 112, 114, 116. The ozone enriched air then passes into an outlet chamber 54 which directs the flow of ozone downward through intake 36 leading to the initial mixing chamber 35. The combined flow of ozone and the gas withdrawn from the wastewater lift station are output to the linear reaction chamber 40.

In the preferred embodiment, the linear reaction chamber 40 constitutes at least 30 to 50 linear feet of 6 inch diameter plastic corrugated drain tubing. The periodic corrugations along this pipe contribute to a non-laminar flow of the gas traveling through the pipe to insure a repeated, intimate mixing of the components of the gas with the ozone generated by apparatus 38. This length of tubing provides the mixed gas and ozone with sufficient interaction time to permit the complete degradation of the noxious components of the gas withdrawn from the wastewater handling facility so that the gas exiting from outlet 42 generally has no discernible noxious components. At a minimum, the noxious components of the gas should be reduced by about an order of magnitude. The level of ozone generated by the ozone generating apparatus 38 can be controlled through the controls on electrical power supply section 52, as well as by a remote sensor 43 located near outlet 42 to insure that negligible ozone is emitted through outlet 42 to the atmosphere.

Although the present invention has been described in detail with respect to the specific preferred embodiment, it is anticipated that alterations and modifications thereof will be apparent to those skilled in the art which are nevertheless encompassed by the present invention as defined by the following claims. In particular, while only a single installation is illustrated, it will be appreciated that a plurality of such installations could be included in a single wastewater collection system, and the operation and control of the apparatus could be coordinated to achieve enhanced benefits.

What is claimed is:

1. Apparatus for eliminating the emission of noxious or malodorous components from a flow of gas, the apparatus comprising:
   a gas suction apparatus coupled to a source of gas having a noxious or malodorous component, the gas suction apparatus including an outlet,
   a gas mixing chamber coupled to the outlet of the gas suction apparatus to receive the flow of gas,
   an ozone generation apparatus having an outlet coupled to the gas mixing chamber for introducing a controlled flow of ozone into the gas mixing chamber to mix with the gas having the noxious or malodorous component, and
   a reaction conduit coupled to an outlet of the gas mixing chamber to receive the mixed gas and ozone, the reaction conduit having surface features on its inner surface assuring turbulent flow of the gasses through the length of the conduit, and being of sufficient length to assure substantial decomposition and removal of the noxious and malodorous components from the flow of gas, the reaction conduit having an outlet.

2. The apparatus of claim 1 further comprising a control coupled to the gas suction apparatus for regulating the volume of gas withdrawn from the source of gas having a noxious or malodorous component.

3. The apparatus of claim 1 further comprising a regulator coupled to the ozone generation apparatus for controlling the amount of ozone generated for reaction with the gas withdrawn from the source of gas having a noxious or malodorous component.

4. The apparatus of claim 3 further comprising a sensor situated in the reaction conduit adjacent the outlet of the reaction conduit and coupled to the regulator for monitoring the level of ozone to avoid overproduction by the ozone generation apparatus.

5. The apparatus of claim 1 further comprising a heater situated in the reaction conduit for elevating the temperature of the gasses flowing through the conduit to a level sufficient to reduce any remaining ozone in the flow gas.

6. The apparatus of claim 1 further comprising a filter situated at an inlet to the ozone generator apparatus for filtering moisture and particles from the flow of air employed to produce the flow of ozone.

7. The apparatus of claim 1 wherein said reaction conduit comprises at least about thirty feet of plastic pipe having corrugations along the length thereof of an amplitude sufficient to ensure continued intimate mixing of the gasses output from the ozone generation apparatus and the gas suction apparatus.

8. Apparatus for eliminating the emission of noxious or malodorous components from a flow of gas, the apparatus comprising:
   a gas suction apparatus coupled to a source of gas within a confined space, the gas having a noxious or malodorous component, the gas suction apparatus including an outlet,
   a gas mixing chamber coupled to the outlet of the gas suction apparatus to receive the flow of gas,
   an ozone generation apparatus having an outlet coupled to the gas mixing chamber for introducing a controlled flow of ozone into the gas mixing chamber to mix with the gas having the noxious or malodorous component, and
   a reaction conduit coupled to an outlet of the gas mixing chamber to receive the mixed gas and ozone, the reaction conduit having surface features on its inner surface assuring turbulent flow of the gasses through the length of the conduit, and being of sufficient length to assure substantial decomposition and removal of the noxious and malodorous components from the flow of gas, the reaction conduit having an outlet directing the flow of gas into the general atmosphere outside said confined space.

* * * * *